United States Patent [19]

Hayashi

[11] Patent Number: 5,731,863
[45] Date of Patent: Mar. 24, 1998

[54] OPHTHALMIC APPARATUS FOR INSPECTING A REFRACTIVE POWER OF AN EYE

[75] Inventor: Akihiro Hayashi, Toyokawa, Japan

[73] Assignee: Nidek Company, Ltd.

[21] Appl. No.: 636,134

[22] Filed: Apr. 22, 1996

[30]  Foreign Application Priority Data

Apr. 21, 1995 [JP] Japan .................. 7-120610

[51] Int. Cl.⁶ ............................................ A61B 3/02
[52] U.S. Cl. ................................. 351/222; 351/239
[58] Field of Search ........................... 351/200, 205, 351/222, 227, 229, 239; 364/413.05, 449

[56]  References Cited

U.S. PATENT DOCUMENTS

| | | | |
|---|---|---|---|
| 5,416,540 | 5/1995 | Hayashi | 351/239 |
| 5,444,504 | 8/1995 | Kobayashi et al. | 351/237 |
| 5,490,098 | 2/1996 | Kardon | 351/200 |

FOREIGN PATENT DOCUMENTS

| | | |
|---|---|---|
| 0186953 | 7/1986 | European Pat. Off. . |
| 0568081A1 | 11/1993 | European Pat. Off. . |
| 4124056A1 | 1/1993 | Germany . |
| 4221289A1 | 1/1993 | Germany . |
| 3-15893 | 4/1991 | Japan . |
| 5-184538 | 7/1993 | Japan . |
| 5210458 | 8/1993 | Japan . |
| 2267159 | 11/1993 | United Kingdom . |

*Primary Examiner*—Huy Mai
*Attorney, Agent, or Firm*—Rossi & Associates

[57]  ABSTRACT

An ophthalmic apparatus providing a subjective refractive power measuring device for respectively placing optical elements in inspection windows and inspecting refractive powers of eyes to be examined, on a subjective basis, an object indicating device for presenting an object to each eye to be examined, an optometry program designing device for designing an optometry program for activating each of the subjective refractive power measuring device and the object indicating device, and a program executing device for executing the optometry program. The optometry program designing device includes a display device having a screen for inputting the optometry program, an object input device for inputting an object to be presented to a person to be examined, through the input screen, an automatic input device for automatically inputting at least either of an item to be measured by the subjective refractive power measuring device and an auxiliary lens used therefor, based on the input object, and a modifying device for modifying the item set by the automatic input device through the use of the input screen.

10 Claims, 5 Drawing Sheets

OPHTHALMIC APPARATUS FOR INSPECTING A REFRACTIVE POWER OF AN EYE

BACKGROUND OF THE INVENTION

1. Field of the Invention

The present invention relates to an ophthalmic apparatus for subjectively inspecting a refractive power of each eye to be examined and visual performance.

2. Description of the Related Art

An ophthalmic apparatus provided with a subjective refractive power inspecting device for placing various optical elements in front of eyes to be examined is normally used to make a prescription for spectacle lenses for correcting refractive ametropia of the eyes to be examined and inspect visual performance of the eyes to be examined.

In recent years, the ophthalmic apparatus has been multi-featured so that various inspections can be performed. Further, the diversity of items to be inspected has been increased. Therefore, there has been proposed an apparatus of a type wherein inspection procedures are programmed to operate a subjective refractive power inspecting device so that even an examiner who has little expert knowledge about and experience in optometry, is able to easily examine the eyes.

An optometry program is one obtained by integrating basic optometry or inspection procedures in the apparatus. However, the inspection procedures differ in various ways according to inspection purposes. As an apparatus capable of inputting and setting the inspection procedure program by an examiner, an ophthalmic apparatus for inputting an optometry program through a display provided with a windowing feature has been disclosed in Japanese Patent Laid-Open No. Hei 5-184538 (1993), for example. According to the disclosed apparatus, an inspection object(which is also called "chart"), an auxiliary lens and eyes to be examined are successively set by an input means for each measuring step through a measuring program set screen displayed on the display and each set measuring procedure is stored in a storage or memory means.

However, the aforementioned apparatus has a problem that respective items must be selectively input one by one to specify or designate the type of object, the type of auxiliary lens, the contents of measurements, each eye to be examined, etc. upon program-inputting the inspection items, so that much time is required upon program input.

Further, a problem also arises that since the number of the input items of the apparatus are restricted, a precise inspection cannot be carried out.

SUMMARY OF THE INVENTION

With the foregoing problems in view, it is therefore a technical object of the present invention to provide an ophthalmic apparatus capable of easily and promptly inputting an inspection procedure program and thereby inputting a precise inspection program.

According to one aspect of this invention, for achieving the above object, there is provided an ophthalmic apparatus comprising: a subjective refractive power measuring device for respectively placing optical elements in inspection windows and inspecting refractive powers of eyes to be examined, on a subjective basis; object indicating means for presenting an object to each eye to be examined; optometry program designing means for designing an optometry program for activating each of the subjective refractive power measuring device and the object indicating means; and program executing means for executing the optometry program, the optometry program designing means including display means having a screen for inputting the optometry program; object input means for inputting an object to be presented to a person to be examined, through the input screen; automatic input means for automatically inputting at least either of an item to be measured by the subjective refractive power measuring device and an auxiliary lens used therefor, based on the input object; and modifying means for modifying the item set by the automatic input means through the use of said input screen.

According to the present invention, since an optometry program can be input while an examiner is looking at a list of the contents on an optometry program input screen and various items can be automatically set by simply selecting an object, an inspection procedure program can be easily and promptly input.

Further, a masked object can be also set by a program upon object selection and hence a precise inspection program can be executed.

Furthermore, since the contents of a comment displayed on an inspection screen can be freely renewed and set upon program input, the optometry that further conforms to the same lines as the examiner, can be carried out.

The above and other objects, features and advantages of the present invention will become apparent from the following description and the appended claims, taken in conjunction with the accompanying drawings in which a preferred embodiment of the present invention is shown by way of illustrative example.

BRIEF DESCRIPTION OF THE DRAWINGS

The present invention will be described with reference to the accompanying drawings in which.

DETAILED DESCRIPTION OF THE PREFERRED EMBODIMENTS

Figure 1:
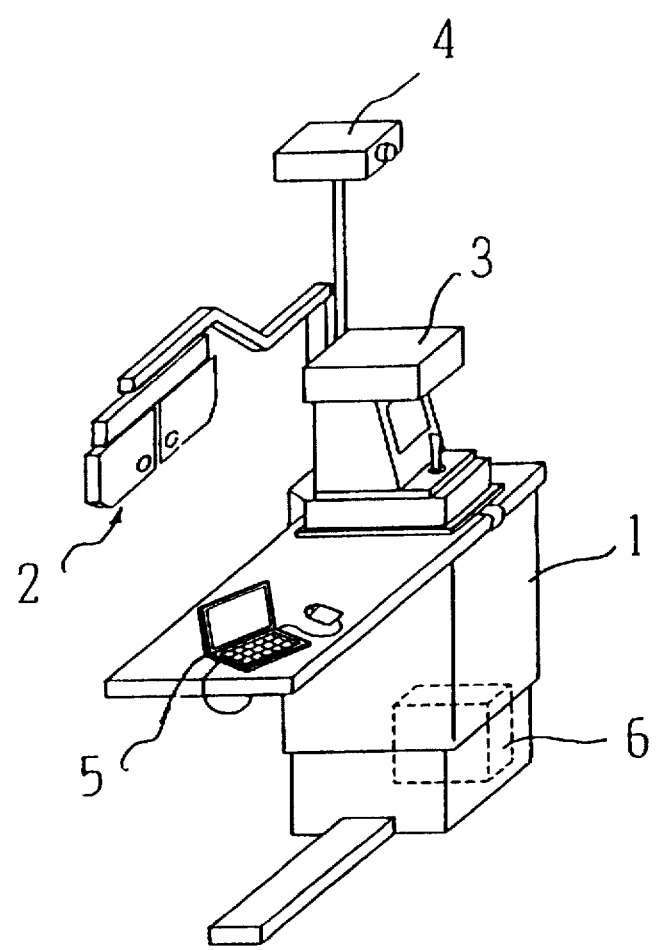
FIG. 1 is an external view showing a schematic configuration of an ophthalmic apparatus according to an embodiment of the present invention.

One embodiment of the present invention will hereinafter be described with reference to the accompanying drawings. FIG. 1 is an external view showing a schematic configuration of an ophthalmic apparatus according to the embodiment of the present invention.

The ophthalmic apparatus according to the present embodiment roughly comprises an optometry table 1 placed between a person to be examined and an examiner, a subjective refractive power measuring device 2 for placing various optical elements in left and right inspection windows by electromotive switching, an objective refractive power measuring device 3 mounted on a movable tray and slidable on the optometry table 1, a projection type object indicating device 4 for presenting a testing object, a controller 5 for operating the subjective refractive power measuring device 2 and the projection type object indicating device 4 and inputting an optometry program, and a relay unit 6 for performing a communication relay between the respective devices.

Configurations of Respective Components (Controller)

Figure 2:
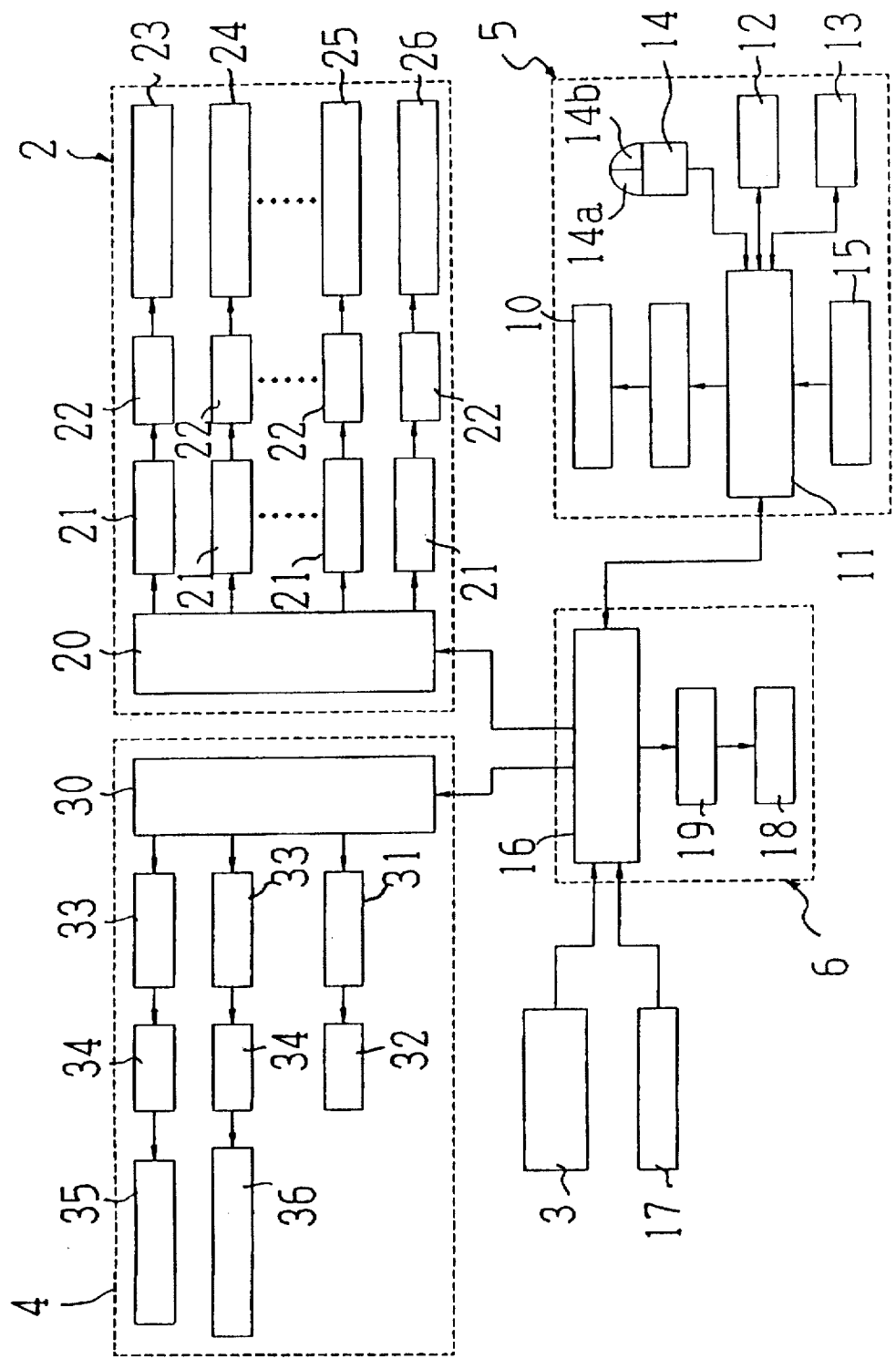
FIG. 2 is a block diagram for describing a control system of the ophthalmic apparatus shown in FIG. 1.

FIG. 2 is a block diagram for describing a control system of the ophthalmic apparatus. Reference numeral 10 indicates a display composed of an LCD or the like. The display 10 displays various screens such as optometry information etc. by switching and displays a plurality of screens so as to overlap each other. Reference numeral 11 indicates a microcomputer circuit, which controls the entire controller 5 and the display 10 and sends input command and program signals to the respective devices. A memory 12 for storing therein control programs such as an optometry information screen, an optometry program input screen, etc. to be displayed on the display 10 and a memory 13 for writing and storing a plurality of optometry programs are electrically connected to the microcomputer circuit 11.

Reference numeral 14 indicates a mouse which functions as an input means for inputting a command using a pointer displayed on the display 10. The mouse 14 has two click switches 14a and 14b provided on the left and right sides thereof. Reference numeral 15 indicates a keyboard used to input characters and the like. The mouse 14 and the keyboard 15 are also electrically connected to the microcomputer circuit 11.

Incidentally, the controller 5 may be configured specifically as a means for controlling the operation of the ophthalmic apparatus and a means for inputting the optometry program. As an alternative, however, a commercially available notebook personal computer with a window display function incorporated therein may be used.

(Relay unit)

A signal output from the microcomputer circuit 11 is input to a microcomputer circuit 16 of the relay unit 6. In response to the signal input to the microcomputer circuit 16, the microcomputer circuit 16 sends a signal about a subjective refractive power to the subjective refractive power measuring device 2 and transmits a signal about an object to the projection type object indicating device 4. Also connected to the microcomputer circuit 16 are the objective refractive power measuring device 3 and a lens meter 17. The microcomputer circuit 16 stores therein measured data sent from the two and thereafter transfers a specified measured data to the microcomputer circuit 11 when a read command signal is input to the microcomputer circuit 16 from the microcomputer circuit 11 on the controller 5 side.

Reference numeral 18 indicates a printer for outputting examined data as prints. Reference numeral 19 indicates a circuit for driving the printer 18.

(Subjective refractive power measuring device)

Reference numeral 20 indicates a microcomputer circuit for controlling the subjective refractive power measuring device 2. The microcomputer circuit 20, which has received the signal about the subjective refractive power from the microcomputer circuit 16, drives one of motors 22 through its corresponding drive circuit 21 to rotate a minor spherical disc 23, a major spherical disc 24, an auxiliary lens disc 25, a cross cylinder disc 26, etc. so as to place a predetermined optical system in a corresponding inspection window.

(Projection type object indicating device)

Reference numeral 30 indicates a microcomputer circuit for controlling the projection type object indicating device 4. The microcomputer circuit 30 supplied with a signal about an object from the microcomputer circuit 16 turns on a lamp 32 through a drive circuit 31 and drives motors 34 through drive circuits 33 so as to rotate an object disc 35 with an object drawn thereon and a mask disc 36, thereby projecting a predetermined inspection object onto an unillustrated screen placed in front of eyes to be examined.

A summary of the input of an optometry program to the apparatus having the above-described structure will be described below with reference to FIGS. 3 through 5.

Figure 3:
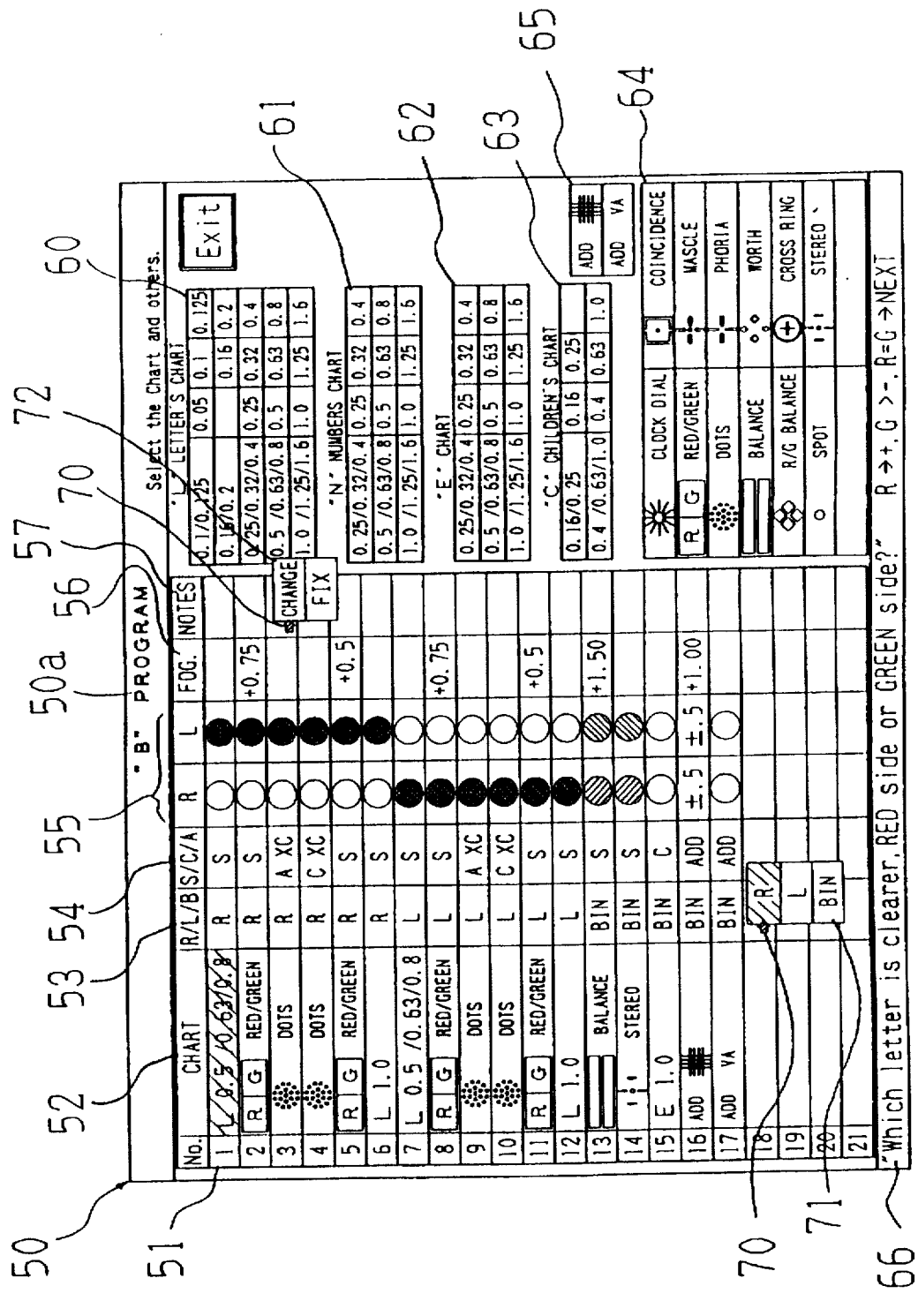
FIG. 3 is a view illustrating one example of a program input screen.

FIG. 3 is a view showing one example of a program input screen 50. A program input operation on the program input screen 50 is as follows. A pointer 70 is shifted on the screen with the mouse 14 and the left click switch 14a of the mouse 14 is pressed so as to specify or point items to be input and the contents for each item.

In the program input screen 50, reference numeral 50a indicates the name of a program mode. In the present example, reference numeral 50a indicates an input screen of a program mode B. Reference numeral 51 indicates an area for setting the contents of a program. Program steps ranging from No. 1 through No. 21 can be input on the drawing. However, subsequent items are scrolled up so that data can be successively input therein. The program steps respectively include setting columns for specifying objects presented by the projection type object indicating device 4, optical elements placed in the inspection windows of the subjective refractive power measuring device 2, etc.

Reference numeral 52 indicates a chart column for setting each presented object, which is specified from an object list group (to be described later) displayed on the right side of the screen.

Reference numeral 53 indicates an examined-eye column for setting eyes to be examined or inspected. When an object is set to the chart column 52, R (right eye) is automatically input to the examined-eye column 53 at the program step No. 1. An examiner places the pointer 70 in the position of the examined-eye column and opens an examined-eye selection screen 71 by pointing at it with the mouse 14, thereby making it possible to re-input L (left eye) and BIN (both eyes) to the examined-eye column 53. In the program steps subsequent to No. 2, the microcomputer circuit 11 reads input information about an eye to be examined at a step immediately before a program step to be set and automatically inputs it. When the program step No. 1 is represented as [R], for example, [R] is automatically set to the program steps subsequent to No. 2 until they are changed.

Reference numeral 54 indicates a measuring item column for setting items to be measured such as the spherical degrees of eyes, the astigmatic degrees of eyes, etc. Each item to be measured (such as an adjustment to the spherical degrees of eyes, an adjustment to the astigmatic degrees of eyes, or the like) is automatically set to the measuring item column so as to correspond to the object set to the chart column 52. Predetermined items to be measured, which are associated with the type of object, have been stored in the memory 12 in advance. The microcomputer circuit 11 sets an object and reads and sets a corresponding item to be measured from the memory 12. Although there are ones unable to correspond to objects univocally as in "DOTS" chart shown in FIG. 3, each item to be measured can be automatically set by programming the initial "DOTS" chart of the same eye based on the setting of the examined-eye column in advance as is the case of an astigmatic axis. The automatically set items to be measured may be changed in a manner similar to the examined-eye column.

Reference numeral 55 indicates an auxiliary lens column for setting auxiliary lenses placed in the left and right inspection windows of the subjective refractive power measuring device 2. The auxiliary lenses employed in the present specification include one and the like as well as a polarizing filter etc. for opening and occluding. Patterns obtained by symbolizing the type of auxiliary lens are placed in "R" (right eye) and "L" (left eye) of the auxiliary lens column 55. This column is automatically set based on the settings of the object column and examined-eye column (in regard to a combination of a specific object and an auxiliary lens, various things are known (refer to Japanese Patent Publication No. Hei 3(1991)-15893)). In the case of a visual acuity test at the program step No. 1, for example, patterns, which means that the right eye is open and the left eye is occluded, are input so as to correspond to the examined eye [R]. The automatically set auxiliary lens may be changed in a manner similar to the examined-eye column.

Reference numeral 56 indicates a fogging column for setting the amount of fogging for applying fogging under the placement of a plus spherical lens at the time of program execution.

Reference numeral 57 indicates a NOTES column used to input comments at each inspection step. The present apparatus has the function of displaying comments for forwarding inspections on the display 10 upon checkup. Comments associated with an object (and a measuring item or the like) are taken out from the contents of the comments stored in the memory 13 and are displayed on a comment display column 66. The NOTES column 57 provided at the lower stage of the program content area 51 is used to change the contents of the comments. When the mouse 14 is driven to open a NOTES window screen 72 shown in FIG. 3 and specify or designate "CHANGE" in the window screen 72, a window screen (not shown) for renewing the comments is further opened, so that the contents displayed on the comment display column 66 can be renewed and changed through the keyboard 15. When the term "FIX" is specified on the window screen 72, the screen returns to the comment's contents stored and set for each object in advance.

Inspection object list groups for selecting objects input to the aforementioned chart column 52 are displayed on the right side of the program content area 51. A character object list 60, a number object list 61, a Snellen object list 62, a children object list 63, and other object list 64 represented by designs of graphic patterns and characters or the like are displayed. Reference numeral 65 indicates an object for near sight. Objects having a plurality of visual value groups can be selected depending on visual values from the object lists 60 through 62. Further, an object placed under the condition in which a lateral mask has been applied every visual values, can be selected.

A program inputting procedure will now be described briefly by the optometry program shown in FIG. 3 as an example.

The program mode B is specified through an unillustrated setting mode screen to open the program input screen 50. When no input is applied to the program content area 51, the color of the chart column 52 at the program step No. 1 is displayed so as to differ from other colors, so that the program step No. 1 is indicated as an input position. As shown in the drawing, character object vision 0.5/0.63/0.8 (which means an object in which visual values 0.5/0.63/0.8 represented in three stages exist within one object) is selected for the chart column 52 at the program step No. 1, the mouse 14 is driven to place the pointer 70 on a [0.5/0.63/0.8] selection key of the character object list 60, after which the left click switch 14a is pressed to select the object. In doing so, the selected object is displayed in the chart column 52 at the program step No. 1 so that the contents of the program are respectively automatically input to the examined-eye column 53, measuring item column 54 and auxiliary lens column 55 provided alongside the chart column 52. Simultaneously, the color of the chart column 52 at the program step No. 2 provided under the program step No. 1 is displayed so as to differ from other colors and the program step No. 2 is next indicated as a program input position.

By simply selecting and specifying objects to be set to the chart columns 52 for every program steps from the right object lists under the operation of the mouse 14 subsequent to the above step, the program's contents are respectively automatically input to the examined-eye column 53, measuring item column 54 and auxiliary lens column 55 provided alongside the chart column 52. A window screen in an amount-of-fogging list screen 74 may be opened so as to input data in the fogging column 56 each time an input is applied to each program step. Alternatively, the data may be input to the fogging column 56 later.

Since [R] is first automatically input to the examined-eye column 53 at the program step No. 7 in the same manner as before, it is corrected or modified to [L]. Thus, the auxiliary lens columns 55 are respectively modified to a closed state of Right and an opened state of Left in accordance with the modification.

Thus, the optometry program can be easily input by simply modifying portions of the objects under the operation of the mouse 14 while the objects being successively selected for the chart columns 52.

The execution of the set optometry program will now be described.

Figure 4:
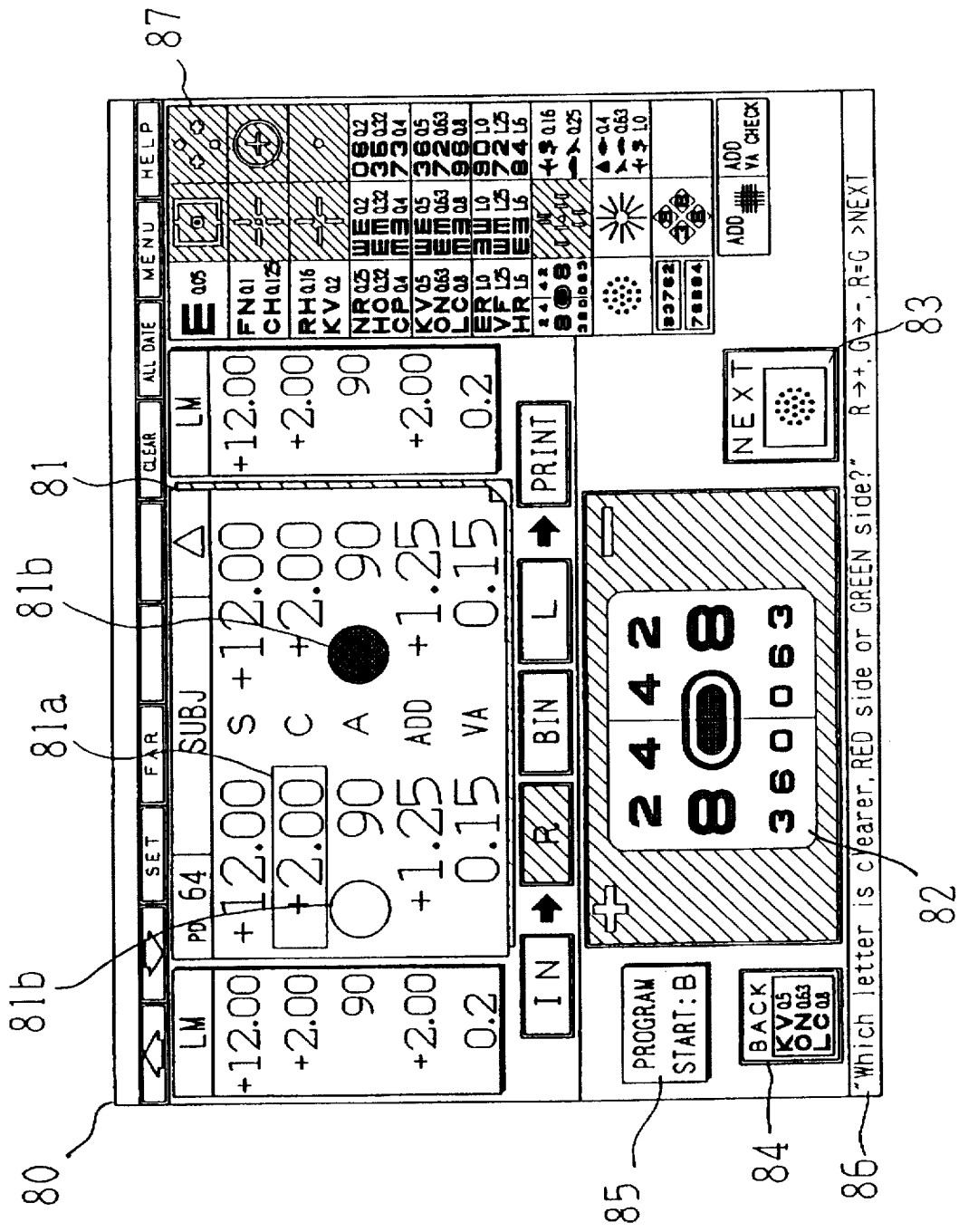
FIG. 4 is a view showing one example of an inspection screen for a display used upon optometry.
Figure 5:
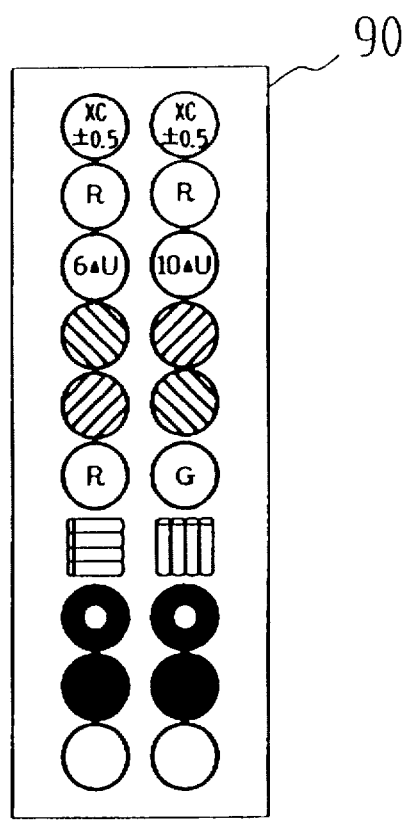
FIG. 5 is a view depicting a list of auxiliary lenses.

FIG. 4 is a view showing one example of an inspection screen 80 displayed on the display 10 upon optometry. Reference numeral 81 indicates an optometry information display portion for displaying optometry information thereon. The optometry information display portion 81 displays the present eye to be examined and measuring items through a frame display 81a and displays the types of auxiliary lenses placed in the left and right inspection windows of the subjective refractive power measuring device 2 through patterns 81b.

Reference numeral 82 indicates an object display portion for displaying the presently-indicated object in the form of a pattern. Reference numeral 83 indicates a program forward key used to proceed to the next program step upon program optometry. The contents of an object at the next program step are displayed by patterns so as to provide visual easy recognition thereof. Reference numeral 84 indicates a program back key used when the program step returns to the immediately preceding program step. Reference numeral 85 indicates a program start key used to select an optometry program and input a program start command.

Reference numeral 86 indicates a comment display portion for displaying the contents of comments associated with a presented object. Upon execution of the optometry program, the comments inputted as a program are displayed on the comment display portion 86. The inputting of the contents of a question made to a person to be examined and the contents of operation as programs makes it possible to give help to an examiner or the like who has little knowledge about optometry upon optometry.

Reference numeral 87 indicates object groups in which objects to be inspected are displayed in pattern or design form.

The program optometry is executed as follows. In order to start the program mode B selected at present, the mouse 14 is driven to select and specify the program start key 85. The microcomputer circuit 11 reads the optometry program stored in the memory 13. Further, the microcomputer circuit 11 effects respective displays on the display 10 based on the contents of the program and allows the projection type object indicating device 4 to present an object (an object masked when it is necessary to use the mask). Furthermore, the microcomputer circuit 11 causes the subjective refractive power measuring device 2 to place the auxiliary lenses in their corresponding inspection windows.

When it is desired to change a numeric value for a measuring item displayed on the frame display 81a in each individual optometry step, the pointer 70 is placed in the object display portion 82 and the left click switch 14a or the right click switch 14b of the mouse 14 is pressed to change an increase or decrease in numeric value at a predetermined step.

The program forward key 83 is selected by the pointer 70 under the operation of the mouse 14 to proceed to the next program step. Further, the program back key 84 can be selected to return to the already-executed immediately preceding program step as needed.

A description has been made of the execution of optometry based on the optometry program as described above. However, the present apparatus can manually examine the eyes as a matter of course. In regard to an inspection screen used upon manual operation, the sections used for the program forward key 83 and the program back key 84 are made blank in the screen example shown in FIG. 4. The mouse 14 is driven to select an object to be presented from the object groups 87. The frame display 81a of the optometry information display portion 81 can be shifted under the operation of the mouse 14 so as to select and specify an eye to be examined and items to be measured. The type of auxiliary lens is selected in the following manner. That is, the pointer 70 is shifted to the pattern 81b, where the left click switch 14a of the mouse 14 is pressed so that a window screen of an auxiliary lens list 90 shown in FIG. 5 is displayed on the upper screen of the object groups 87 so as to overlap each other. Thus, a desired auxiliary lens can be selected from this window screen under the operation of the mouse 14 likewise.

Having now fully described the invention, it will be apparent to those skilled in the art that many changes and modifications can be made without departing from the spirit or scope of the invention as set forth herein.

What is claimed is:

1. An ophthalmic apparatus comprising:
   a subjective refractive power measuring device for respectively placing optical elements in inspection windows and inspecting refractive powers of an eye to be examined, on a subjective basis;
   chart presenting means for presenting a test chart to the eye to be examined;
   optometry program designing means for designing an optometry program for activating each of said subjective refractive power measuring device and said chart presenting means; and
   program executing means for executing the optometry program;
   wherein said optometry program designing means includes display means having an input screen for inputting the optometry program;
   chart input means for inputting a test chart to be presented to the eye to be examined, through said input screen;
   automatic input means for automatically inputting at least either of an item to be measured by said subjective refractive power measuring device and an auxiliary lens used therefor, based on the input test chart; and
   modifying means for modifying the item set by said automatic input means through the use of said input screen.

2. An ophthalmic apparatus according to claim 1, wherein said chart input means includes information on applying a mask to the test chart being inputted.

3. An ophthalmic apparatus according to claim 1, further comprising comment setting means for setting a comment displayed on an on-optometry display, based on the type of the input chart.

4. An ophthalmic apparatus according to claim 3, further comprising comment renewing means for renewing the comment set by said comment setting means.

5. An ophthalmic apparatus according to claim 1, wherein the input screen of said display means includes a designing section for designing each of a right side and a left side of the eye to be examined, a right-left eye input means for automatically inputting the same designation as the right-left designed by the designing section until the designation is changed.

6. An ophthalmic apparatus comprising:
   a subjective refractive power measuring device for respectively placing optical elements in inspection windows and inspecting refractive powers of an eye to be examined, on a subjective basis;
   chart presenting means for presenting a test chart to the eye to be examined;
   optometry program designing means for designing an optometry program for activating each of said subjective refractive power measuring device and said chart presenting means; and
   program executing means for executing the optometry program;
   wherein said optometry program designing means including display means having an input screen for inputting the optometry program;
   chart input means for inputting a test chart to be presented to the eye to be examined, through said input screen;
   automatic input means for automatically inputting an item to be measured by said subjective refractive power measuring device and an auxiliary lens used therefor, based on the input test chart; and
   fogging input means for inputting additional spherical degree to apply fogging in the inspection window of said subjective refractive power measuring device.

7. An ophthalmic apparatus according to claim 6, wherein said chart input means includes information on applying a mask to the test chart being inputted.

8. An ophthalmic apparatus according to claim 6, further comprising comment setting means for setting a comment displayed on an on-optometry display, based on the type of the input chart.

9. An ophthalmic apparatus according to claim 8, further comprising comment renewing means for renewing the comment set by said comment setting means.

10. An ophthalmic apparatus according to claim 6, wherein the input screen of said display means includes a designing section for designing each of a right side and a left side of the eye to be examined, a right-left eye input means for automatically inputting the same designation as the right-left designed by the designing section until the designation is changed.

* * * * *